(12) United States Patent
Garraud et al.

(10) Patent No.: US 10,634,742 B2
(45) Date of Patent: Apr. 28, 2020

(54) MAGNETIC NANOPARTICLE SPECTROMETER

(71) Applicant: University of Florida Research Foundation, Inc., Gainesville, FL (US)

(72) Inventors: Nicolas Garraud, Gainesville, FL (US); Carlos Rinaldi, Gainesville, FL (US); David P. Arnold, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 10 days.

(21) Appl. No.: 15/766,638

(22) PCT Filed: Oct. 7, 2016

(86) PCT No.: PCT/US2016/056074
§ 371 (c)(1),
(2) Date: Apr. 6, 2018

(87) PCT Pub. No.: WO2017/062821
PCT Pub. Date: Apr. 13, 2017

(65) Prior Publication Data
US 2019/0064289 A1 Feb. 28, 2019

Related U.S. Application Data

(60) Provisional application No. 62/238,797, filed on Oct. 8, 2015.

(51) Int. Cl.
*G01R 33/12* (2006.01)
*G01N 24/08* (2006.01)
(Continued)

(52) U.S. Cl.
CPC .......... *G01R 33/1276* (2013.01); *A61B 5/055* (2013.01); *G01N 24/08* (2013.01); *A61B 5/0515* (2013.01)

(58) Field of Classification Search
CPC ... G01R 33/1276; A61B 5/055; A61B 5/0515; G01N 24/08
See application file for complete search history.

(56) References Cited

U.S. PATENT DOCUMENTS 6,791,319 B2  9/2004 Hiroshima
8,350,566 B2  1/2013 Ohyu et al.
(Continued)

OTHER PUBLICATIONS

International Search Report for PCT/US2016/056074 dated Dec. 30, 2016.

*Primary Examiner* — Gregory H Curran
(74) *Attorney, Agent, or Firm* — Thomas Horstemeyer, LLP

(57) ABSTRACT

Disclosed are various embodiments for a system configured to characterize a magnetic response of a sample. The system can comprise an electrical source configured to generate a time-varying current supply, an excitation coil system coupled to the electrical source to generate a time-vary magnetic field for application to a sample, and a sensing coil system that senses a magnetic response of the sample in response to the time-varying magnetic field. The sensing coil system can comprise a pick-up coil and a balancing coil that can be translated or rotated. The balancing coil configured to cancel a feed-through induction signal. In another embodiment, the sensing coil system can comprise an adjustable fine-tuning coil that is configured to modify an effect of the cancellation of the feed-through induction signal.

20 Claims, 13 Drawing Sheets

(51) Int. Cl.
*A61B 5/055* (2006.01)
*A61B 5/05* (2006.01)

(56) References Cited

U.S. PATENT DOCUMENTS

| | | |
|---|---|---|
| 2007/0268021 A1 | 11/2007 | Sakakura |
| 2008/0204009 A1 | 8/2008 | Gleich et al. |
| 2008/0204010 A1 | 8/2008 | Crozier et al. |
| 2011/0316526 A1* | 12/2011 | Nisato .................... A61B 5/05 324/202 |
| 2012/0019238 A1 | 1/2012 | Eichardt et al. |

* cited by examiner

MAGNETIC NANOPARTICLE SPECTROMETER

CROSS REFERENCE TO RELATED APPLICATIONS

This application claims priority to co-pending PCT Application No. WO2017/062821, filed Oct. 7, 2017, entitled "MAGNETIC NANOPARTICLE SPECTROMETER," which claims priority to U.S. Provisional Application No. 62/238,797, filed Oct. 8, 2015, entitled "MAGNETIC NANOPARTICLE SPECTROMETER," which are entirely incorporated herein by reference.

STATEMENT REGARDING FEDERALLY SPONSORED RESEARCH OR DEVELOPMENT

This invention was made with government support under grant R21 EB018453 awarded by the National Institutes of Health. The government has certain rights in the invention.

BACKGROUND

Recent developments in magnetic particle imaging (MPI) address the main drawbacks found in nuclear imaging by detecting non-radioactive tracers (i.e., magnetic nanoparticles), while achieving higher resolution in a shorter process time. In addition, magnetic particle spectroscopy has been used to characterize magnetic nanoparticles.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

Figure 1A:
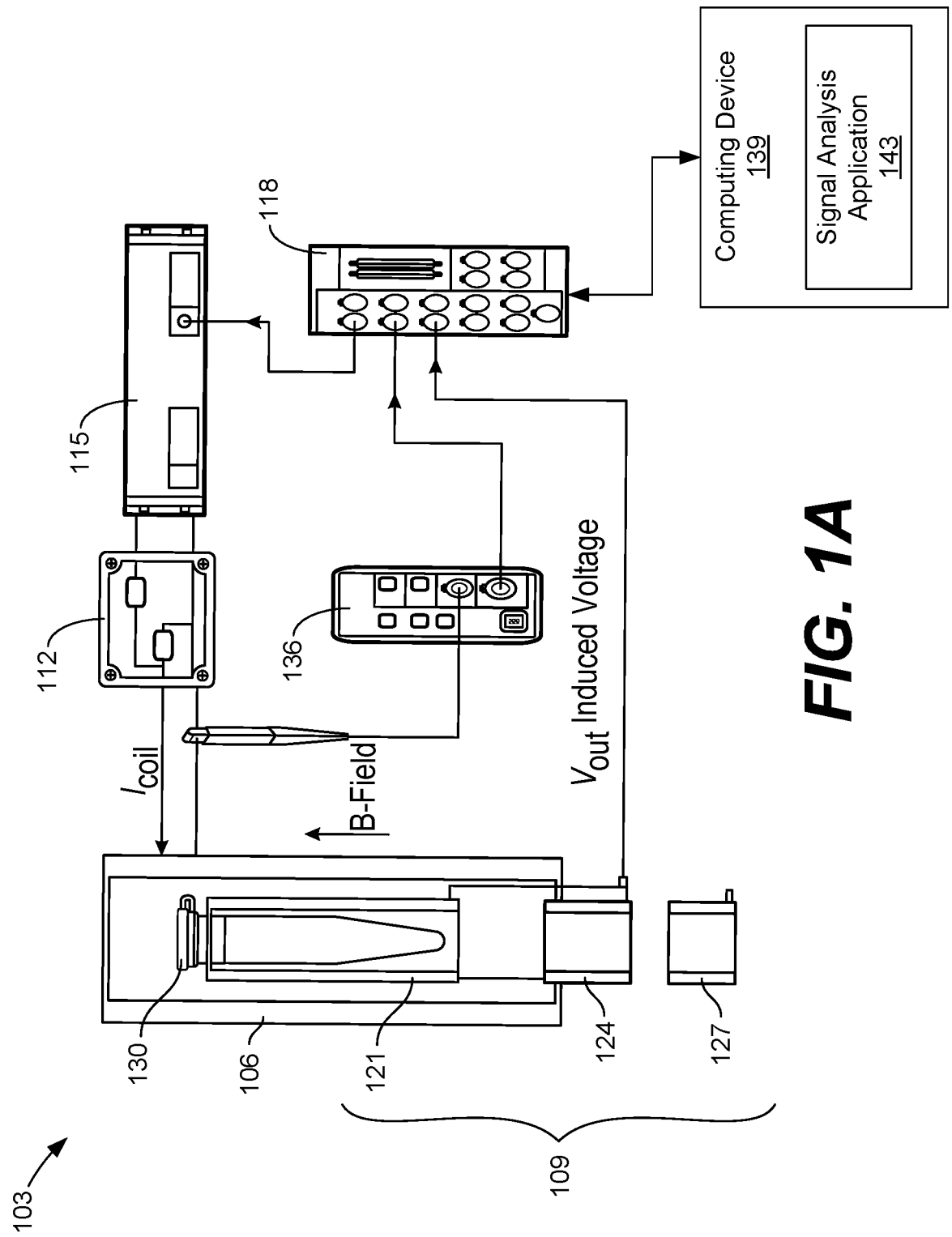
FIG. 1A illustrate a magnetic particle spectrometer system according to various embodiments of the present disclosure.

The drawings illustrate only exemplary embodiments and are therefore not to be considered limiting of the scope of the embodiments described herein, as other equally effective embodiments are within the scope and spirit of this disclosure. The elements and features shown in the drawings are not necessarily drawn to scale, emphasis instead being placed upon clearly illustrating the principles of the exemplary embodiments. Additionally, certain dimensions or positionings may be exaggerated to help visually convey certain principles. In the drawings, similar reference numerals between figures designates like or corresponding, but not necessarily identical, elements.

DETAILED DESCRIPTION

Embodiments of the present disclosure relate to a magnetic particle spectrometer (MPS) system that can be used to characterize linear and nonlinear behavior of magnetic nanoparticle suspensions. Particularly, the embodiments can be used to characterize the suspension dynamic response, both due to relaxation and saturation effects, which depends on the magnetic particles and their environment. The MPS system can apply excitation magnetic fields varying in amplitude and frequency and can be configured for linear measurements (e.g., 1 millitesla (mT) at up to 120 kHz) and nonlinear measurements (e.g., 50 mT at up to 24 kHz). Time-resolved data acquisition at up to 4 MS/s combined with hardware and software-based signal processing can allow for wide-band measurements up to 50 harmonics in nonlinear mode. By cross-calibrating the instrument with a known sample, the instantaneous sample magnetization can be quantitatively reconstructed. As non-limiting examples, validation of the two MPS modes has been performed for iron oxide and cobalt ferrite suspensions, exhibiting respectively Néel and Brownian relaxation.

The development of MPS systems is motivated by a desire to assess magnetic suspension suitability for magnetic particle imaging (MPI). MPI is an emerging biomedical imaging technique addressing drawbacks found in nuclear imaging by using non-radioactive tracers (i.e., the magnetic nanoparticles), with theoretically higher resolution in a short process time. MPI detects nanoparticle density spatially by locally probing their dynamic magnetization in a spatial selection gradient field. Various embodiments can assess both particle suspension relaxation and saturation, related to their performance for MPI. Further information regarding MPI is provided in P. W. Goodwill, Rev. Sci. Inst., 2012, 83, 033708, which is incorporated by reference herein in its entirety.

The embodiments described herein can be used in applications in which the characterization of a magnetic nanoparticle's response to a varying magnetic field is of interest. Such applications include, but are not limited to, MPI, thermal cancer therapy, magnetically-triggered drug delivery, biosensing, measurement of fluid properties (e.g. viscosity, coagulation), pathogen detection, real-time cardiovascular imaging, stem cell tracking and hyperthermia.

The embodiments have several advantages over existing solutions. For instance, the embodiments include innovative features such as a measurement of full time-series data, instead of discrete spectral components using a lock-in amplifier; multi-mode attenuation/cancellation of the primary excitation signal (about −93 dB attenuation of the feed-through); and an estimation of the instantaneous magnetization of the suspension, instead of just the induced voltage.

The dynamic response of the magnetic suspension depends on the strength and frequency of the applied magnetic field. Nonlinearity in response can increase with magnetic field amplitude because of particle magnetic saturation, while relaxation effects become more evident with increasing frequency. Observing and quantifying these phenomena is relevant to the study of the dynamic response of magnetic suspensions, to improve their synthesis, or to infer on their suitability for diverse applications, such as MPI.

The various embodiments of the present disclosure can operate in two modes, herein referred to as "linear DMS" (dynamic magnetic susceptibility) and "nonlinear MPS". At low applied field amplitudes, linear DMS can probe the linear magnetization regime of the nanoparticles, similarly to AC susceptometry. The response to a sinusoidal time-varying magnetic field can be a sinusoidal magnetic moment change, from which the complex magnetic susceptibility, characteristic of the suspension rotational dynamics, can be determined. At higher applied field amplitudes, nonlinearity can appear in the sample response due to magnetic saturation of the suspension. The magnetization can saturate, yielding sharper, non-sinusoidal voltage changes when the magnetization flips. The measured spectrum can present odd harmonics of the fundamental frequency, characteristic of the suspension magnetic nonlinearity. This nonlinear MPS mode can characterize the nanoparticle suspension rotational dynamics, both in amplitude and in frequency, assessing both saturation and relaxation effects.

In addition, the embodiments enable characterization of motionless samples and at a high magnetic field amplitude. Accordingly, the various embodiments do not need any motion of the sample to obtain precise measurements, which is an advantage over other commercially available equipment. In addition, a motionless sample addresses several existing problems such as easing the MPS system design, decreasing system cost, permitting faster measurements, enabling additional instrumentation controls (e.g., temperature control, controlled ambient, etc.), and enabling a coil system to apply a rotating magnetic field instead of a uniaxial magnetic field.

Measurements obtained using the various embodiments of the MPS system described herein can evaluate the suitability of different particles for various applications and provide feedback to improve their synthesis. The embodiments of the present disclosure also relate to a novel specialized coil system for feed-through signal cancellation (i.e. cancellation of direct induction from an excitation coil), signal analysis with remaining feed-through subtraction, and magnetization determinations with system calibrations.

In addition, with regard to high field amplitudes, the limitations in field amplitudes in conventional AC susceptometry can be addressed by the use of a power amplifier coupled with capacitor sets to adapt, by impedance matching, and increase, by resonance, the current delivered to the coil. The ability to use high magnetic field allows for the nonlinear behavior characterization of the particle suspension.

In the following paragraphs, the embodiments are described in further detail by way of example with reference to the attached drawings. In the description, well known components, methods, and/or processing techniques are omitted or briefly described so as not to obscure the embodiments. Turning to the drawings, a general description of exemplary embodiments of a magnetic particle spectrometer system and its components are provided, followed by a discussion of the operation of the system.

FIG. 1A illustrates a magnetic particle spectrometer (MPS) system 103. The MPS system 103 shown in FIG. 1A is representative of one arrangement of components in an example MPS system. However, other arrangements are within the scope of the embodiments including arrangements in which certain components shown in FIG. 1A are omitted and/or arrangements in which certain components are rearranged relative to each other or replaced by other components. The MPS system 103 includes, for example, an excitation coil 106, a sensing coil system 109, a capacitor circuit 112, a power amplifier 115, a data acquisition system 118, a vial 130, a current probe 136, and a computing device 139. In the illustrated embodiment, among others, the excitation coil 106 can be electrically coupled to the capacitor circuit 112 and the capacitor circuit 112 can be, in turn, electrically coupled to the power amplifier 115. The excitation coil 106 can comprise a gapped solenoid excitation coil. In some embodiments, the excitation coil 106 can be directly coupled to the power amplifier 115, in which case the capacitor circuit 112 can be omitted.

The excitation coil 106 can be configured to induce a time-varying magnetic field that is applied to the contents of the vial 130. The excitation coil 106 can be embodied as a coil of magnet wire optimized to provide a large homogeneous magnetic field, while keeping its resistance and inductance low. In this scenario, the power amplifier 115 can provide more current at high frequencies. The capacitor circuit 112 can comprise a resonant matching circuit implemented using pairs of high-voltage capacitors (e.g. Cornell-Dubilier).

The power amplifier 115 can be embodied as any suitable power amplifier capable of accurately reproducing and amplifying the power of an input signal. One non-limiting example of the power amplifier 115 is the 7224 DC-enabled AC power amplifier manufactured by AE Techron®. In some embodiments, the power amplifier 115 can be omitted and replaced with an electrical source, such as a power supply, a function generator, and other suitable electrical sources.

The sensing coil system 109 can be configured to sense a magnetization of a sample and null out or negate the inductive signal from the excitation coil 106. The sensing coil system 109 can comprise a number of individual coils, some of which are fixed and some of which can be displaced translationally or tilted. In some embodiments, the sensing coil system 109 can entirely be positioned within a cavity of the excitation coil 106. In other embodiments, the sensing coil system 109 can be positioned partially within the cavity of the excitation coil 106 and partially outside of the cavity of the excitation coil 106. The sensing coil system 109 can be embodied as a number of coils of magnet wire, including a pick-up coil 121, a balancing coil 124, and an adjustable fine-tuning coil 127. The pick-up coil 121 can include a cavity for the placement of a nanoparticle sample in a vial 130. The pick-up coil 121 (e.g., AWG 28, 40 turns, diameter 10.5 mm) can be internally molded in epoxy resin to minimize the distance between the pick-up coil 121 and the nanoparticle sample in the vial 130, thereby maximizing the sensitivity to the nanoparticle sample while minimizing feed-through. The vial 130 can comprise a magnetic sample such as a nanoparticle suspension, nanoparticles frozen in a polymer, and other suitable magnetic materials.

The pick-up coil 121 can be electrically coupled to the balancing coil 124. In some embodiments, the balancing coil 124 can be mounted in series and wound in an opposite direction of the pick-up coil 121. In addition, the balancing coil 124 can be fixed in place in order to minimize the sensitivity to displacements.

The adjustable fine-tuning coil 127 can be electrically coupled to the pick-up coil 121 and the balancing coil 124. As described in further detail below, the position of the adjustable fine-tuning coil 127 can be adjusted relative to the balancing coil 124 to modify the effect of signal cancellation provided by the balancing coil 124. The adjustable fine-tuning coil 127 can also be magnetically (inductively) coupled to the pick-up coil 121 and the balancing coil 124. The adjustable fine-tuning coil 127 can be closed on itself, translated, and/or rotated.

The sensing coil system 109 can be electrically coupled to the data acquisition system 118 to measure an induced voltage generated in the sensing coil system 109. The data acquisition system 118 can comprise a current probe 136 to measure the current being supplied to the excitation coil 106 and a magnetic field sensor to measure the time-varying magnetic field. One non-limiting example of the current probe 136 is the TCP305A probe with TCPA300 amplifier manufactured by Tektronix®. The data acquisition system 118 can measure electrical or physical phenomenon, such as voltage, current, temperature, pressure, sound, and other suitable signals. The data acquisition system 118 can comprise of sensors, various analog and digital electronic components, and a processor. One non-limiting example of the data acquisition system 118 is the PCI-6115 simultaneous sampling multifunction data acquisition (DAQ) unit manufactured by National Instruments™. In some embodiments, the data acquisition system 118 generates a sinusoidal input signal to the power amplifier 115, and the power amplifier 115 amplifies the signal, which is applied to the excitation coil 106.

In some embodiments, the data acquisition system 118 can be coupled to or installed within the computing device 139. Thus, the computing device 139 can control and monitor the operations of the data acquisition system 118 and store data captured by the data acquisition system 118.

The computing device 139 can comprise, for example, a processor-based system such as a desktop computer, a laptop computer, tablet computer, or other computing device with similar capability. The computing device 139 can include a display. The display can comprise, for example, one or more devices such as liquid crystal display (LCD) displays, gas plasma-based flat panel displays, organic light emitting diode (OLED) displays, electrophoretic ink (E ink) displays, LCD projectors, or other types of display devices, etc.

The computing device 139 can be configured to execute various applications such as a signal analysis application 143 and/or other applications. The signal analysis application 143 can be executed in the computing device 139, for example, for signal analysis processing, such as remaining feed-through subtraction. The remaining feed-through can refer to feed-through after hardware cancellation and before software substation. To this end, the signal analysis application 143 can comprise, for example, an internet browser, a dedicated application, etc., and the user interface can comprise a network page, an application screen, etc.

Figure 1B:
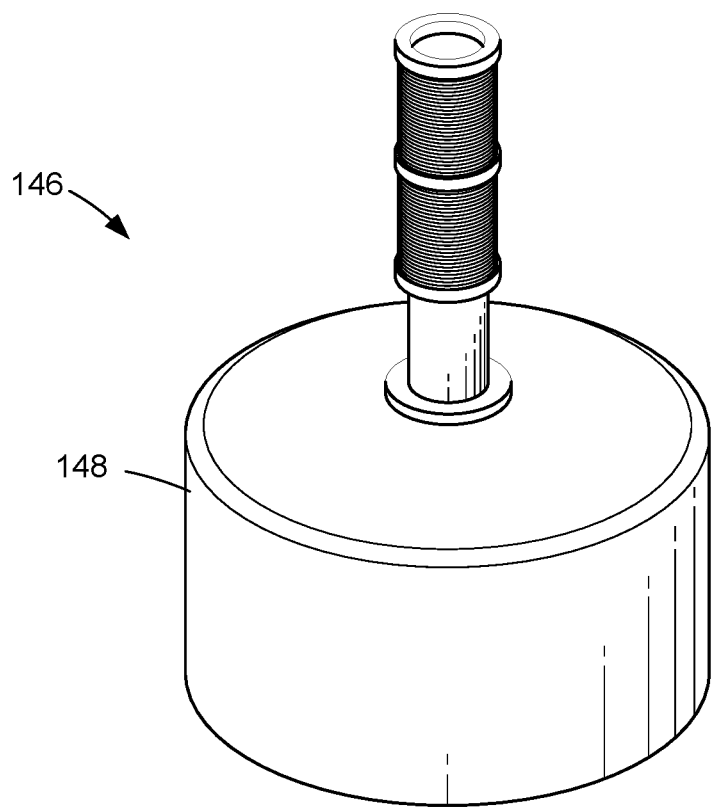
FIGS. 1B and 1C illustrate a perspective view of an assembly of the magnetic particle spectrometer system and an exploded view of part of the assembly, respectively according to various embodiments of the present disclosure.
Figure 1C:
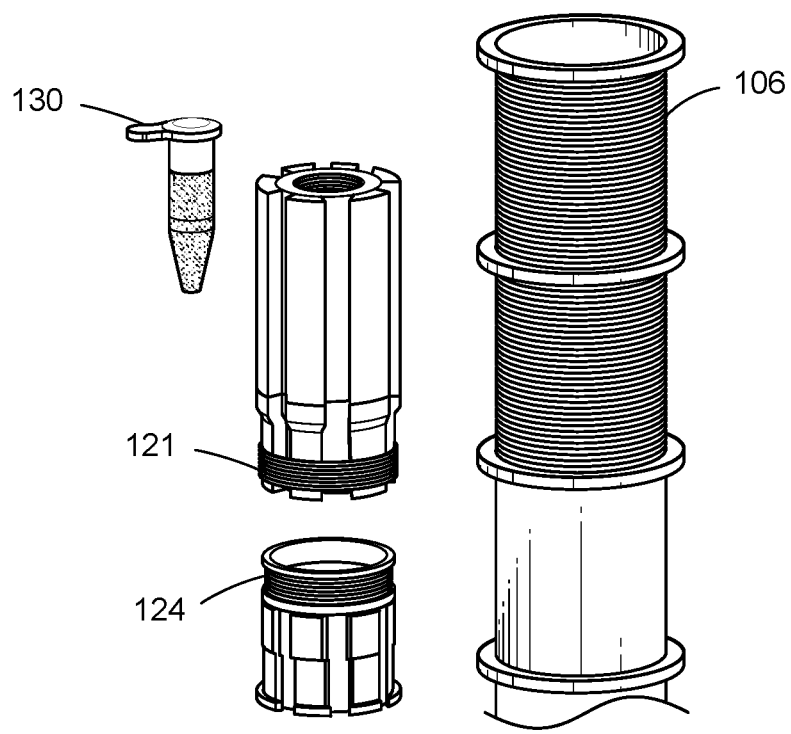

Turning to FIGS. 1B and 1C, shown is a perspective view of an exemplary embodiment of an assembly 146 comprising the excitation coil 106 and the sensing coil system 109. As illustrated in FIG. 1B, the sensing coil system 109 is positioned within a cavity of the excitation coil 106. In addition, the excitation coil 106 can be attached to a base structure 148. FIG. 1C shows an enlarged exploded view of the excitation coil 106, the pick-up coil 121, the balancing coil 124, and the vial 130. As discussed above, the vial 130 is positioned within a cavity of the pick-up coil 121. Further, the pick-up coil 121 and the balancing coil 124 can be positioned within a cavity of the excitation coil 106.

Referring between FIGS. 1A through 1C, a general description of the operation of the various components of the MPS system 103 is provided. The MPS system 103 can provide a spatially uniform, sinusoidally time-varying magnetic field to a nanoparticle suspension in the vial 130. On non-limiting example of the vial 130 is a 1 mL Eppendorf vial. The magnetic field can range from, for example (but not limited to), 1 to 50 mT, at frequencies from 1 to 120 kHz. The field can be generated by the excitation coil 106 with sinusoidal current supplied via the power amplifier 115 fed by the data acquisition system 118. The nanoparticles can rotate in response to the applied magnetic field, inducing a change in magnetic flux detected by the sensing coil system 109. The induced voltage and driving current can be recorded simultaneously by the data acquisition system 118.

In some embodiments, among others, the excitation coil 106 can be formed to have electrical characteristics and dimensions optimized to provide a large homogeneous magnetic field, while keeping its resistance and inductance low. In this scenario, the power amplifier 115 can provide more current at high frequencies. As one non-limiting example, the excitation coil 106 dimensions can be American Wire Gauge (AWG) 19, 206 turns, diameter 30 mm, 73 mm long. In this example, the embodiment can provide a homogeneous magnetic field of about 3 mT/A, 5% inhomogeneity over the sample volume and a resistance of 0.58 Ω and an inductance, 400 μH.

The data acquisition system 118 can output the sinusoidal excitation waveform to the power amplifier 115, and the excitation coil 106 can be either directly connected to the power amplifier 115 terminals or connected via a resonant matching circuit in order to achieve higher field amplitudes. The direct connection mode can provide wide-band measurements in the linear DMS mode, with maximum field amplitudes of 50 mT for frequencies up to 5 kHz, 10 mT up to 30 kHz, and 1 mT up to 120 kHz.

In the nonlinear MPS mode, the resonant matching circuit can be implemented using pairs of high-voltage capacitors and designed for a current gain of about 3 at discrete frequencies. In this way, the MPS system 103 can reach 50 mT at 3, 10.8, 16, 19.6 and 24 kHz. Measurement results at 3 kHz and 24 kHz are described herein using resonant matching circuits. The input excitation current shows at most −50 dBc/Hz phase noise at 1 Hz offset from the carrier and total harmonic distortion of better than −63 dB across all cases, confirming high spectral purity of the excitation magnetic field.

Other embodiments can include different time variations of the magnetic field such as square waveforms, triangular waveforms, or other non-sinusoidal waveforms. Other embodiments can include aperiodic waveforms. Additional embodiments can include rotating magnetic fields or other spatially varying field patterns.

In another embodiment, the MPS system 103 can comprise an alternative excitation coil system for applying magnetic fields in different spatial axes with different timing. One non-limiting example would be a rotating magnetic field. In this example, the excitation coil system can comprise more than one coil system in different directions for a 3D field excitation.

The embodiments of the present disclosure comprise various signal measurements and feed-through cancellation techniques. As described above, the nanoparticle rotation is detected by the sensing coil system 109, which is designed in part to finely cancel out an effect of the feed-through-induced signal. The specificity resides in both the construction of the sensing coil system 109 and the data process to recover the magnetization information. In some embodiments, the data acquisition system 118 can simultaneously measure the current delivered to the excitation coil 106 and the nanoparticle response as measured by the sensing coil system 109. The excitation coil current can be measured by the current probe 136 to assess the reference phase of the excitation magnetic field.

Thus, a primary design challenge for the sensing coil system 109 is to negate the direct induction from the excitation coil 106 to the sensing coil system 109 (called "feed-through"). Ideally, the sensing coil system 109 would only measure the rate of change of the magnetic moment of the nanoparticle suspension in the vial 130. To mitigate feed-through, the sensing coil system 109 can comprise of three coils: the pick-up coil 121 that can sense the sample magnetization change, the balancing coil 124, and the adjustable fine-tuning coil 127. In one example embodiment, the sensing coil system 109 can have a self-resonance frequency of about 1 MHz. This can set the upper frequency bound for measurements.

As discussed above, the pick-up coil 121 can be internally molded in epoxy resin, e.g. AWG 28, 40 turns, diameter 10.5 mm, to help minimize the distance between the pick-up coil 121 and the sample and help maximize the sensitivity to the nanoparticle sample while minimizing feed-through. The balancing coil 124 can be electrically coupled in series with the pick-up coil 121, although being formed from magnet wire wound in an opposite direction. The excitation field induces a voltage with opposite phase that counteracts the main induction from the pick-up coil 121. The balancing coil 124, which is relatively sensitive to displacement, can be fixed at 25 mm from the pick-up coil 121 to avoid interaction with the sample. Furthermore, to allow fine cancellation adjustments, the adjustable fine tuning coil 127 is placed relatively close to (e.g. within a predefined distance) to the balancing coil 124.

In one embodiment, the adjustable fine tuning coil 127 comprises a movable short-circuited fine-tuning coil placed close to a fixed balancing coil. In this embodiment, the adjustable fine-tuning coil 127 is inductively coupled to both the excitation coil 106 and the balancing coil 124, which modifies the balancing and further reduces the feed-through.

Figure 1D:
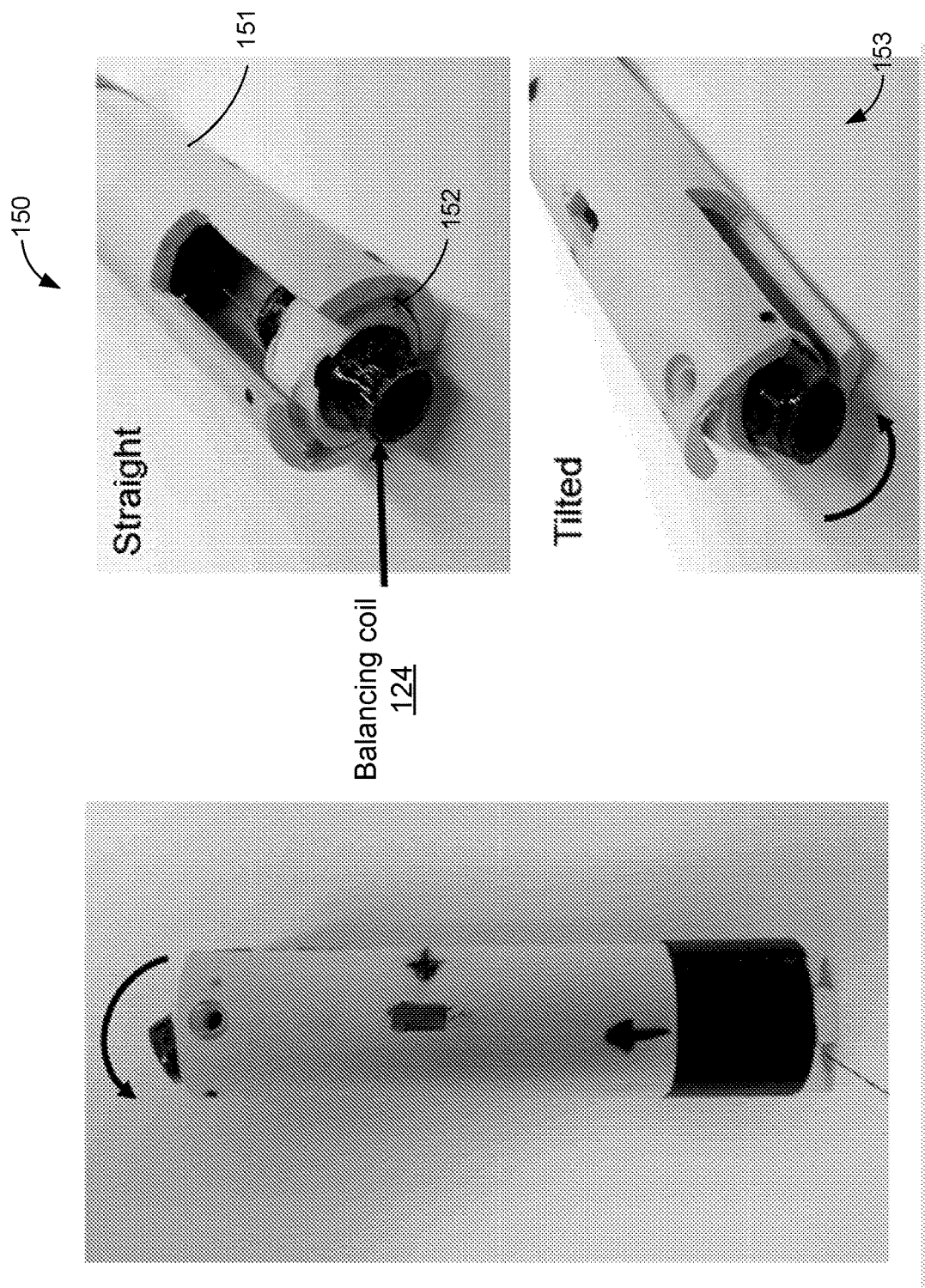
FIG. 1D illustrates a structure for tilting a balancing coil according to various embodiments of the present disclosure.

With reference to FIG. 1D, shown is another embodiment in which the balancing coil 124 can be tilted to enable feed-through cancellation and omits the use of the adjustable fine-tuning coil 127. As discussed above, the balancing coil 124 can be coupled in series with the pick-up coil 121. In FIG. 1D, reference number 150 points to an illustration of the balancing coil 124 positioned within one end of a cylindrical structure 151 and in a substantially straight (i.e. vertical) orientation along a longitudinal axis of the cylindrical structure 151. In some embodiments, the cylindrical structure 151 can be positioned partially within a cavity of the excitation coil 106 and partially within a cavity of the base structure 148 (FIG. 1B). The cylindrical structure 151 can comprise a pair of slots at the end, which provides a channel of space for the balancing coil 124 to move as it is being tilted. In addition, the balancing coil 124 can be positioned inside of and coupled to a ring 152. The ring 152 can be mechanically attached to the end of the cylindrical structure 151 via at least one axis. The mechanical attachment of the ring 152 can enable the balancing coil 124 to rotate about the at least one axis.

Reference number 153 points to an illustration of the balancing coil 124 tilted at an angle after the ring 152 has been rotated. The pick-up coil 106 and balancing coil 124 can be designed for smaller sample volume (200 µL). Accordingly, the coil disposition is more symmetric than before when compared to the excitation coil 106. The balancing coil 124 can physically be tilted, which can enable feed-through cancellation without tuning the coil. The magnetic flux through the balancing coil depends on its axial position (the field spatially varies and decays near the excitation coil edges), and on its angular position (projected area decays with the angle).

As one non-limiting example, the dimensions of the balancing coil 124 are diameter=8.05 mm, L=16 mm, 80 turns AWG 34, 1 layer. The pick-up coil for 200 µL suspension can have dimensions such as diameter=8.5 mm, L=6.9 mm, 64 turns AWG 34, 2 layers. The direct induction from the excitation coil 106 on the pick-up coil 121 alone induced a maximum feed-through about 27.9 V (at 30 kHz, 50 mT). The maximum feed-through was reduced at 60 mV with the straight balancing coil. By tilting the balancing coil 124, the maximum feed-through is further reduced to under 0.61 mV. Table 1 illustrates the balancing characterization:

TABLE 1

|  |  | Pick-up | Pick-up + straight balancing | Pick-up + tilted balancing |
| --- | --- | --- | --- | --- |
| Feed-through | coefficient (mV/A · Hz) | 54.8 | 0.117 | <0.0012 |
|  | maximum (mV) 30 kHz, 50 mT | 27940 | 60 | <0.61 |
| Cancellation | ratio | 1 | 466 | >45800 |
|  | % |  | −99.78% | −99.9998% |
|  | dB | 0 | −53 dB | −93 dB |

Further, the coupling pick-up coil/balancing coil is less than 1.3%. Table 2 illustrates the coil characterization:

|  | Pick-up | Balancing | Sensing system |
| --- | --- | --- | --- |
| R (Ω) | 2.16 | 2.5 | 4.7 |
| L (µH) | 29.14 | 24.47 | 53.59 |
| Coupling with excitation coil | ~11% | ~11% | <1% |

The at least one axis can be coupled to a knob that is positioned outside of the cylindrical structure 151. In this embodiment, the balancing coil 124 can be rotated about the axis in response to a turn of the knob. In another embodiment, among others, the at least one axis can be coupled to an automated mechanical means of rotating the balancing coil 124. As one skilled in the art can appreciate, there are other means of rotating the balancing coil 124.

Figure 1E:
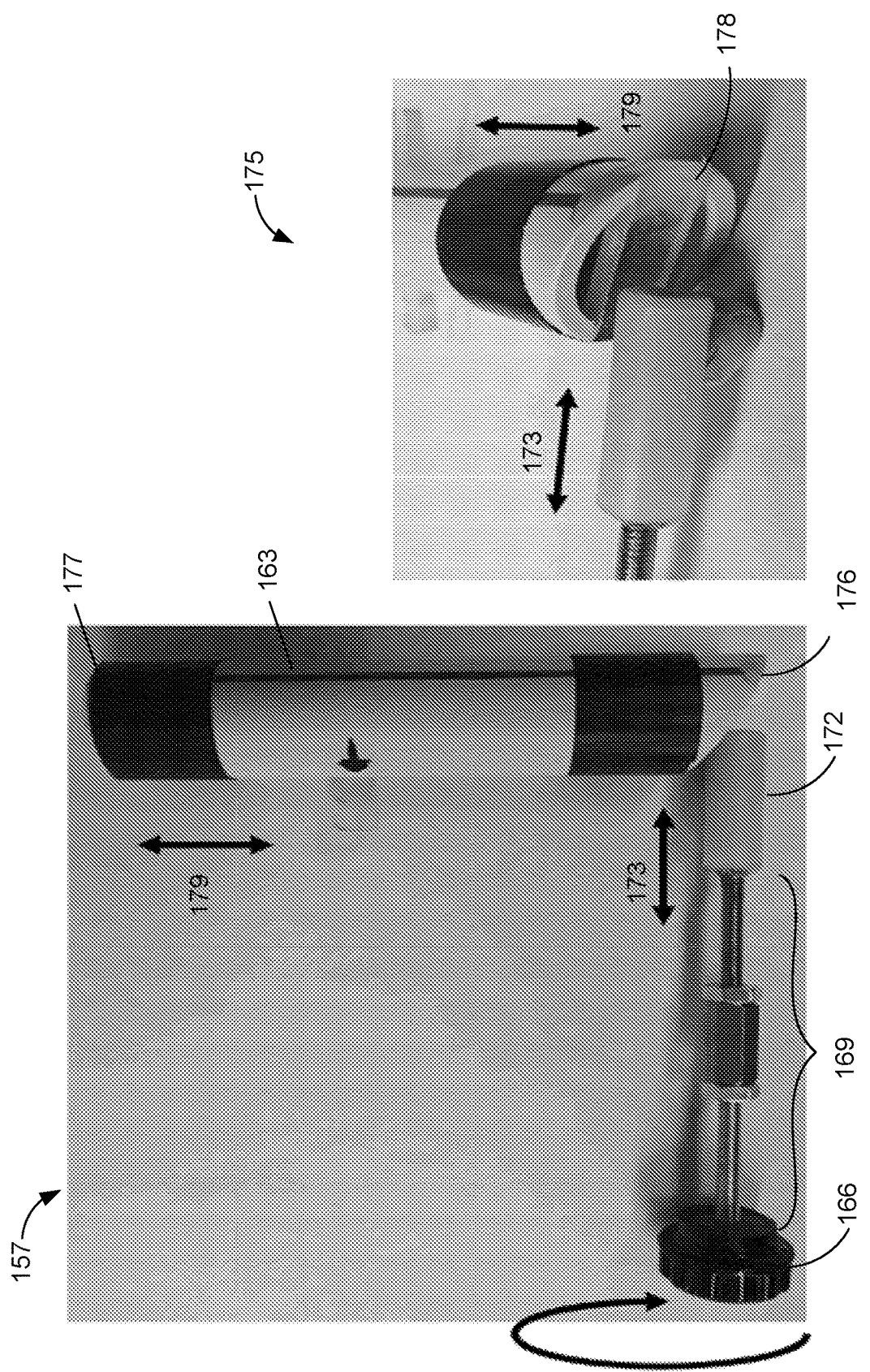
FIG. 1E illustrates a displacement structure for a balancing coil according to various embodiments of the present disclosure.
Figure 1F:
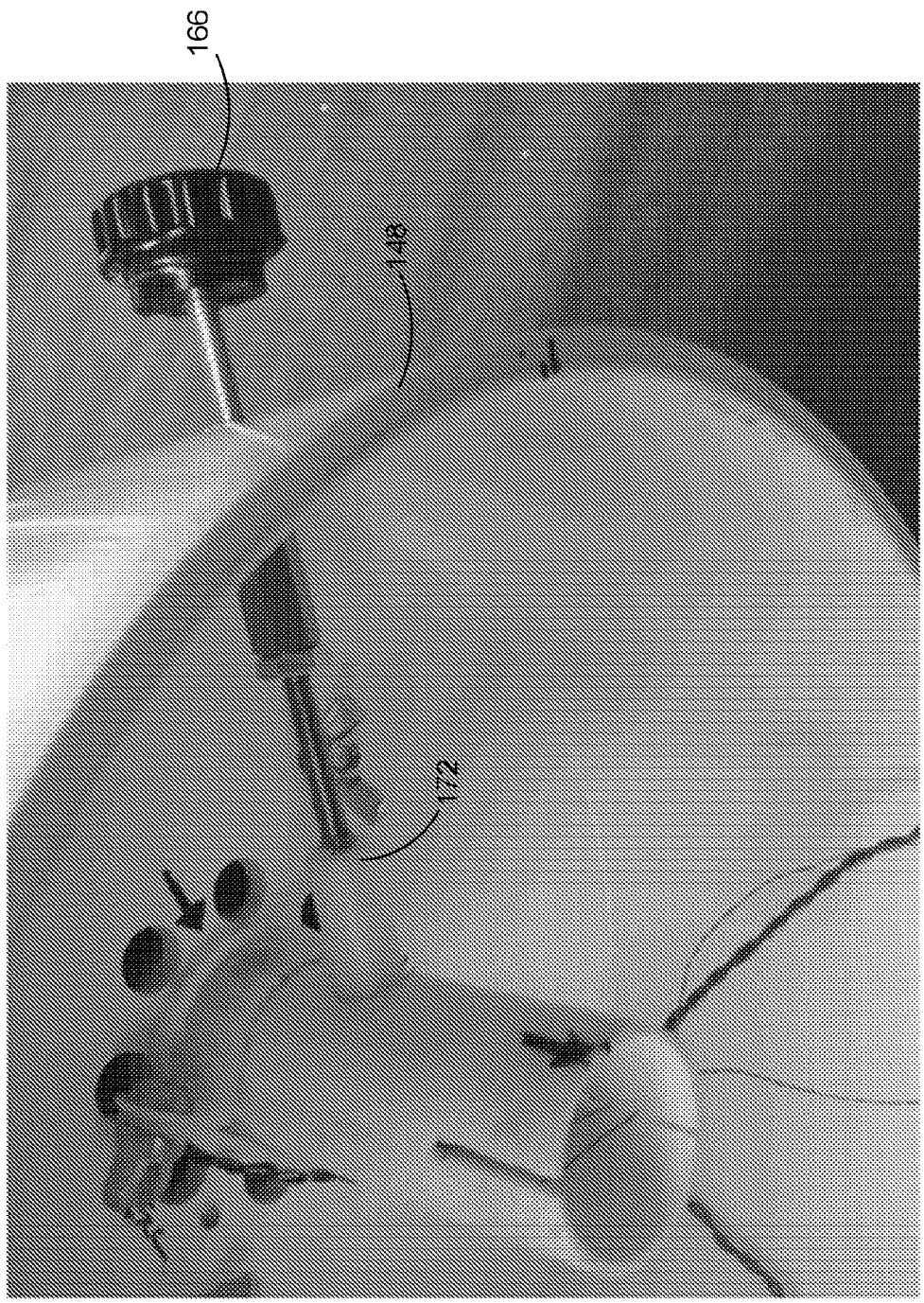
FIG. 1F illustrates a perspective view beneath a base structure of the assembly of the magnetic particle spectrometer system according to various embodiments of the present disclosure.

Turning now to FIGS. 1E and 1F, shown is another embodiment for feed-through cancellation by using positional displacement without tuning the balancing coil 124. This embodiment omits the use of the adjustable fine-tuning coil 127. In FIG. 1E, reference number 157 refers to a plunging structure 160 and an elongated structure 163. The plunging structure 160 comprises a knob 166, a shaft 169, and a plunger 172. In FIG. 1F, the plunging structure 160 is illustrated as being inserted through an opening in the base structure 148 of the assembly 146. As the knob 166 is turned, the shaft 169 can extend to move the plunger 172 along a first axis 173, which moves the plunging structure 160 in or out of the base structure 148. In other embodiments, the plunging structure 160 can be rigid and move as unit along the first axis 173. The elongated structure 163 has a first end 176 and a second end 177, in which the balancing coil 124 can be attached to the second end 177. In some embodiments, aspects of the cylindrical structure 151 can be combined with the elongated structure 163. Thus, the second end 177 of the elongated structure 163 can include various structural components for adjusting an axial position of the balancing coil 124. Accordingly, the various structural components from FIGS. 1D and 1E can be combined and configured to translationally displace and/or tilt the balancing coil 124.

Reference number 175 points to an illustration in which the elongated structure 163 comprises a ramp 178 at the first end 176. The ramp 178 can be in contact with the plunger 172. As the plunger 172 moves along the first axis 173, the plunger 172 can be forcibly slid along the ramp 178 to push the elongated structure 163 up and down along a second axis 179 that is substantially perpendicular to the first axis 173. Accordingly, the elongated structure 163 can be moved up and down along the second axis 179 with a suitable level of precision. By moving the elongated structure 163 along the second axis 179, the feed-through can be adjusted as the balancing coil 124 is moved along the second axis 179.

Embodiments of the present disclosure comprise signal processing techniques for determining instantaneous magnetization. For the data reported herein, the first 0.25 s of all measurements were discarded to eliminate any transients from the electronics. For the linear mode, the sampling rate was set at approximately 30 times the excitation frequency (the data acquisition system imposes discrete sampling frequencies) and up to 5 seconds of data was used (minimum of 2500 cycles). For the nonlinear mode, 1 second of data was used (minimum of 3000 cycles) with a sampling rate ≥100 times the excitation frequency so that at least 50 harmonics can be extracted.

In addition to the sensing coil system 109, which can minimize feed-through at the hardware level, additional feed-through can be cancelled numerically during the post-processing using the signal analysis application 143. In some embodiments, among others, the signal analysis application 143 can comprise two measurements being performed sequentially without ($v_{blank}(t)$) and with ($v_{sample}(t)$) the sample present. The fast Fourier transform (FFT) can be applied to both signals (bin width in the FFT spectrum is approximately 1 Hz in all cases) generating frequency-domain spectra $\tilde{V}_{blank}(f)$ and $\tilde{V}_{sample}(f)$, each represented by phasor amplitudes $A_j$ and phases $\varphi_j$. From here on, only the FFT coefficients at the excitation frequency $f_0$ and subsequent N−1 harmonics are considered; all other FFT coefficients are discarded, which acts to filter the relevant signal information. Next, the $\tilde{V}_{blank}$ phasor coefficients are subtracted from the $\tilde{V}_{sample}$ phasor coefficients to obtain $\tilde{V}_{suspension}$. The time-domain voltage induced by the suspension can then be reconstructed, which is also linked to the derivative of the magnetic moment m(t):

$$v_{suspension}(t) = \sum_{k=1}^{N} A_k \sin(2\pi k f_0 t + \varphi_k) = -\frac{d\Phi(t)}{dt} = -\frac{1}{2\pi K_{pickup}} \frac{dm(t)}{dt}, \quad (1)$$

with $K_{pickup}$ a sensitivity coefficient in A·m²/V·s determined experimentally (described later). The instantaneous magnetization M(t) is thus determined by integration of the induced voltage $v_{suspension}(t)$:

$$M(t) = \frac{m(t)}{Vol} = \frac{K_{pickup}}{Volf_0} \sum_{k=1}^{N} \frac{A_k}{k} \cos(2\pi k f_0 t + \varphi_k), \quad (2)$$

where Vol is the volume of the suspension.

In the case of linear DMS, the magnetic moment can be defined by its complex susceptibility $\chi$, the slope of the M-H curve, as $m(t)=Vol\chi H_{ext}(t)$. The susceptibility is projected into its real and imaginary components as $\chi=\chi'-i\chi''=|\chi|e^{-i\psi}$, with $$|\chi| = A_1 \frac{K_{pickup}}{Vol|H_{ext}|f_0}$$

being the amplitude and $$\Psi = \varphi_1 + \frac{\pi}{2}$$

being the phase.

The calibration coefficient $K_{pickup}$, which captures the pick-up coil sensitivity, depends on the pick-up coil 121 and the sample container geometries and is independent of the magnetic sample. This coefficient is determined by measuring the susceptibility spectra of magnetic particle suspensions using both a commercial calibrated AC susceptometer and the linear DMS.

Linear and nonlinear measurements were performed on two in-house magnetic nanoparticle suspensions obtained by thermal decomposition. The first suspension was made of PEG-coated iron oxide nanoparticles with ~55 nm hydrodynamic diameter suspended in water, while the second suspension was made of oleic-acid coated cobalt ferrite nanoparticles with ~22 nm hydrodynamic diameter, ~5 nm core diameter suspended in 1-octadecene.

Figure 2A:
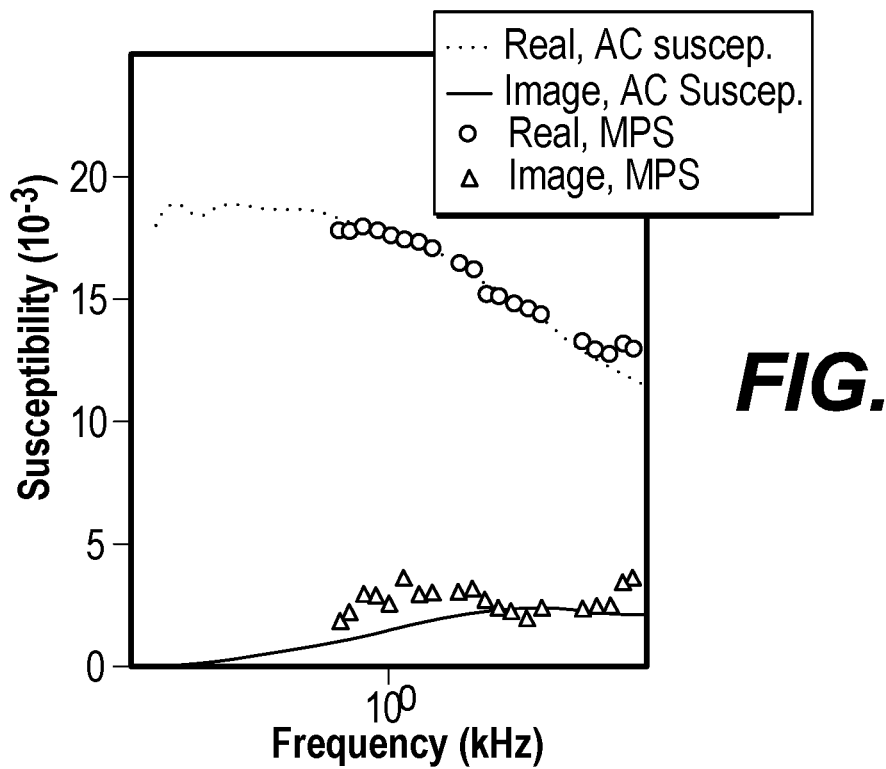
FIGS. 2A and 2B are graphs of linear measurements for iron oxide and cobalt ferrite, respectively, according to various embodiments of the present disclosure.
Figure 2B:
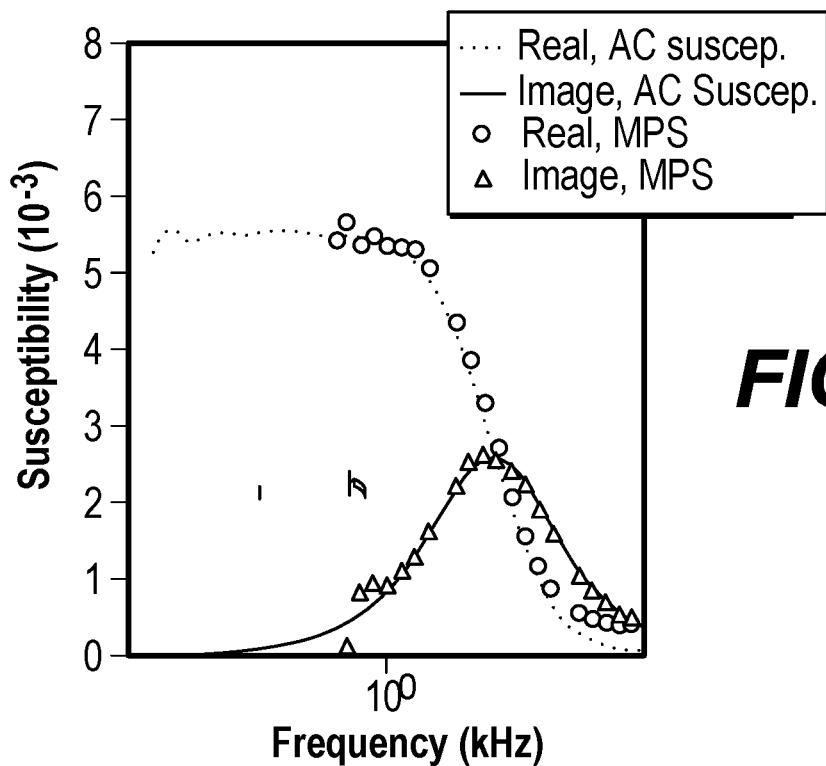

With reference to FIGS. 2A and 2B, shown are graphs of linear DMS characterization measurements for iron oxide and cobalt ferrite particles tested at 1 mT from 500 Hz to 120 kHz. Particularly, FIG. 2A shows a graph of iron oxide particle characterization with linear DMS and FIG. 2B shows a graph of cobalt ferrite particle characterization with linear DMS. Curves show very good agreement with measurements made by AC susceptometry.

The graphs show the in-phase real and out-of-phase imaginary susceptibility component spectra as a function frequency. The markers are MPS measurements, while the solid and dashed lines are measurements from a commercial AC susceptometer (Dynomag, Acreo). Observations were in good agreement between the two instruments for both particles, but because the sensitivity of the inductive sensing method decreases linearly with the frequency, some discrepancy was observed at lower frequencies.

The iron oxide susceptibility spectrum (FIG. 2A) is characteristic of particles relaxing predominantly by the Néel mechanism. The in-phase component remains significantly higher than the out-of-phase component. The cobalt ferrite susceptibility spectrum (FIG. 2B) is characteristic of particles relaxing predominantly by the Brownian mechanism. At low frequency, the in-phase component plateaus with a zero out-of-phase component. Around 9 kHz the in-phase susceptibility drops dramatically while the out-of-phase peaks to its maximum. Finally, both components asymptote to zero as the particle rotations do not respond to overly high frequency excitation field.

Figure 3A:
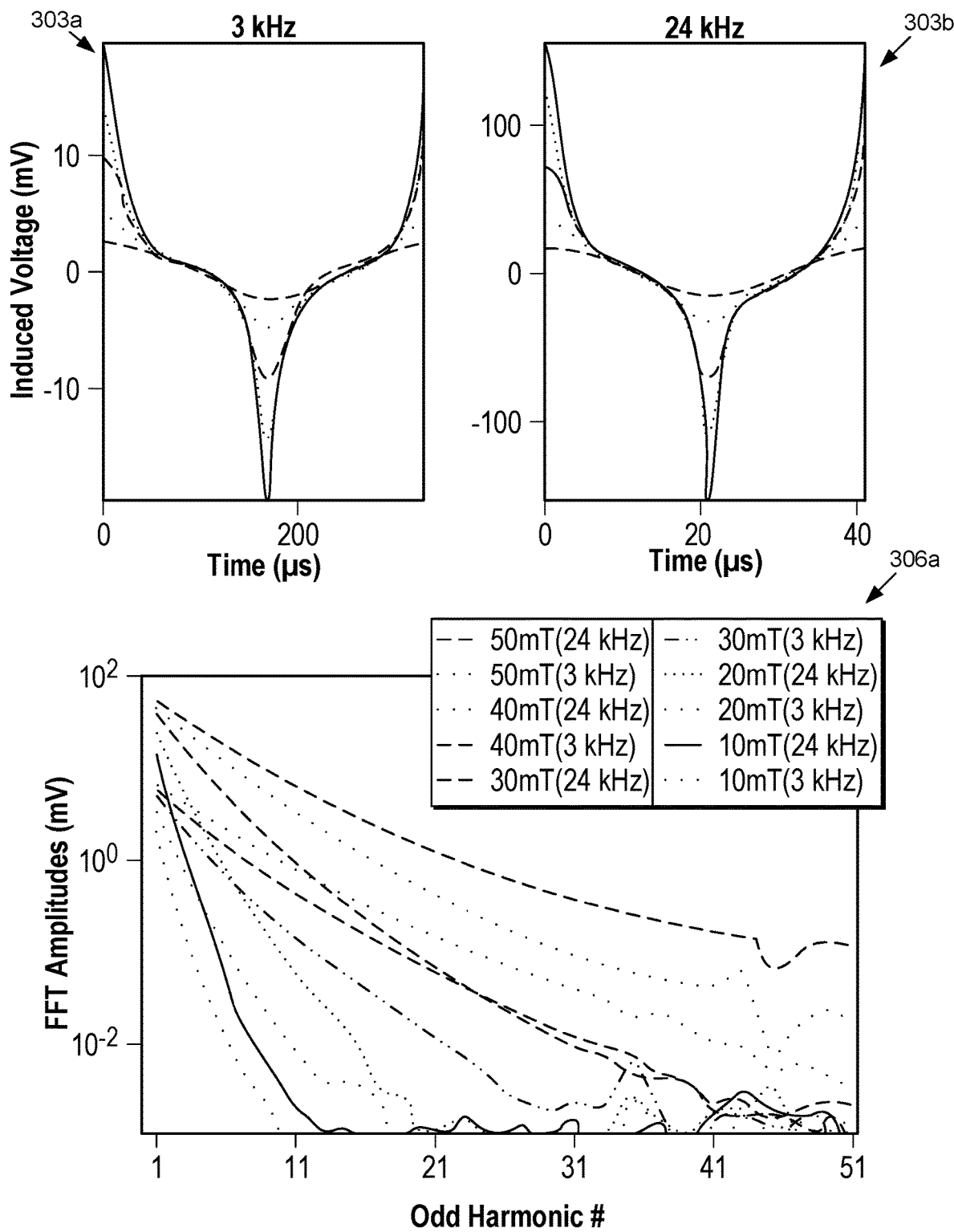
FIGS. 3A through 3D are graphs of nonlinear measurements for iron oxide and cobalt ferrite according to various embodiments of the present disclosure.
Figure 3B:
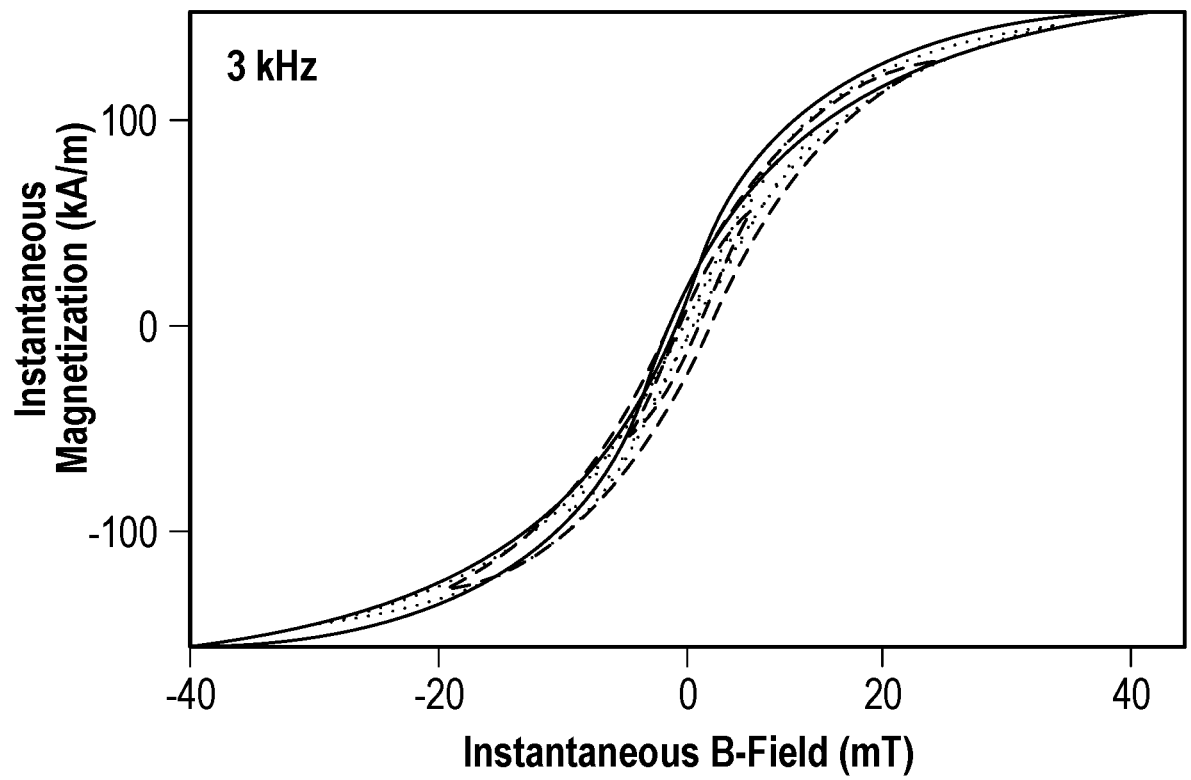
Figure 3B:
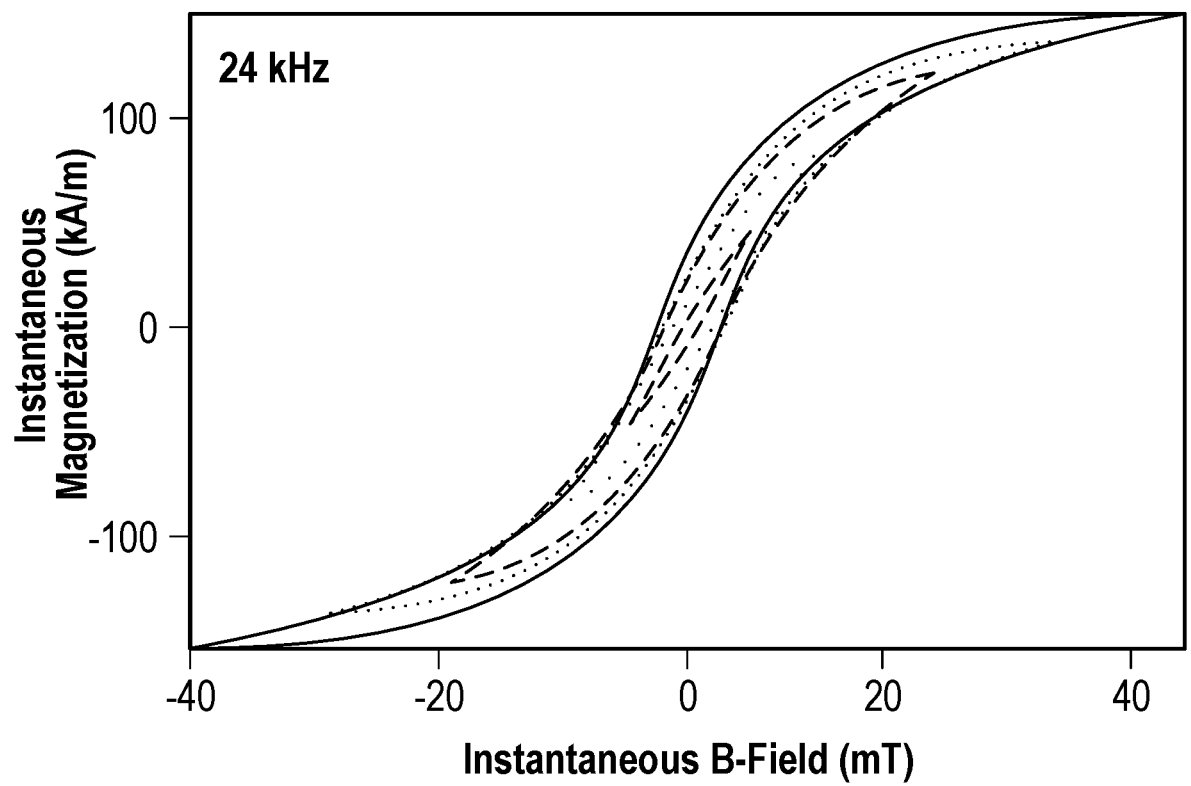
Figure 3C:
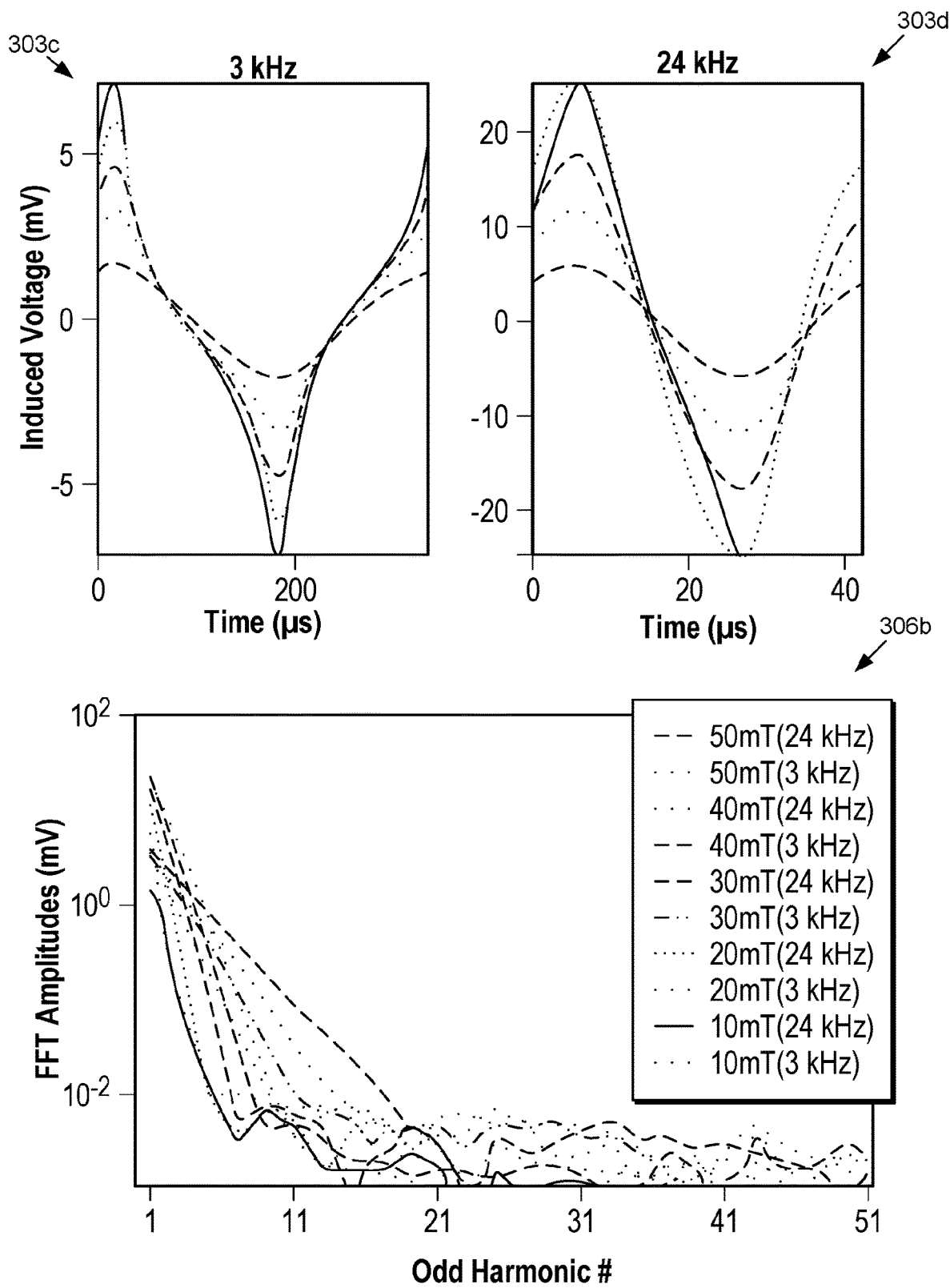
Figure 3D:
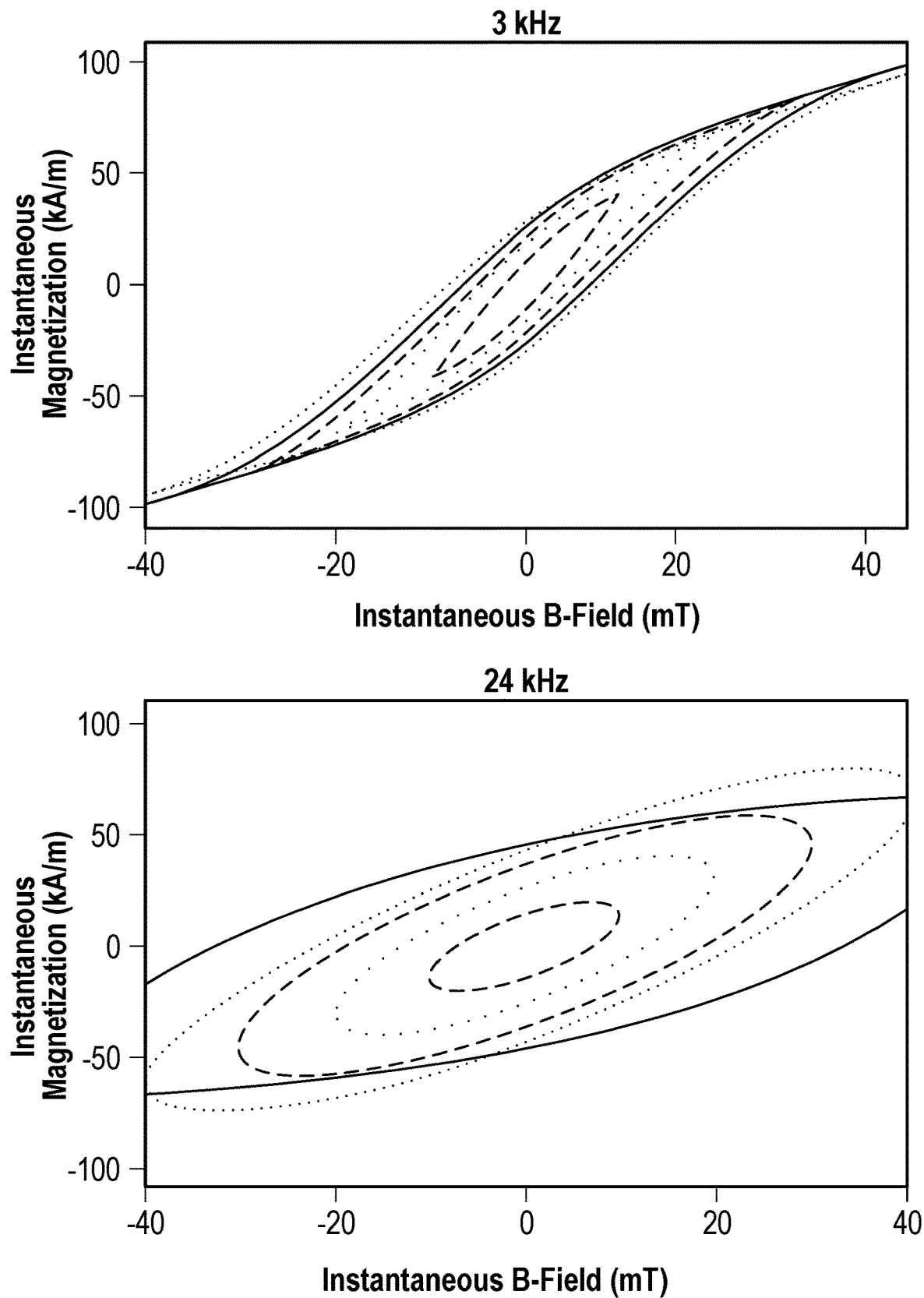

With reference to FIGS. 3A through 3D, shown are graphs of iron oxide and cobalt ferrite nonlinear MPS characterization measurements at 3 kHz and 24 kHz from 5 to 50 mT. Particularly, FIGS. 3A and 3B illustrate graphs of iron oxide nonlinear MPS characterizations at 3 kHz and 24 kHz from 5 to 50 mT and FIGS. 3C and 3D illustrate graphs of cobalt ferrite nonlinear MPS characterizations at 3 kHz and 24 kHz from 5 to 50 mT.

In FIGS. 3A and 3C, references number 303a, 303b, 303c, and 303d include graphs of the measured time-varying induced voltage. In FIGS. 3A and 3C, references number 306a and 306b includes graphs of the voltage FFT spectra. FIG. 3B includes graphs of the corresponding dynamic magnetic hysteresis curves for iron oxide and FIG. 3D includes graphs of the corresponding dynamic magnetic hysteresis curves for cobalt ferrite.

In both cases, the induced voltage increases linearly with magnetic field amplitude. At low excitation fields we see that the voltage response is almost sinusoidal, with few odd harmonics and an almost linear instantaneous magnetization response. However, at high excitation field strength, the voltages change abruptly, resulting in slow decaying FFT spectra and magnetization saturation. For the iron oxide sample, the responses at 3 kHz and 24 kHz are very similar, consistent with Néel relaxing particles with characteristic peak frequency that is much higher than the frequency window of the measurement. The voltage induced at 24 kHz is 8 times higher than at 3 kHz, with the ratio corresponding to the frequency ratio as explained by the magnetic induction phenomena. Moreover, the voltage FFT spectra between 3 kHz and 24 kHz decay at similar rates, providing evidence of induced voltages with the same time variations.

For the cobalt ferrite sample, the responses at 3 kHz and 24 kHz are completely different, consistent with Brownian relaxing particles with a 9 kHz peak frequency that lies between the two studied frequencies. On one hand, the behavior at 3 kHz is similar to the response of the iron oxide suspension, albeit presenting broad voltage peaks and faster voltage FFT decays. On the other hand, the behavior at 24 kHz changes dramatically compare to 3 kHz, which is characteristic of a frequency that exceeds the inverse of the particle's Brownian relaxation time: the voltage switches are even less sharper, the voltage FFT decays more rapidly than at 3 kHz and the instantaneous magnetization reaches a lower magnetization. The two sets of measurements show a shift between two regimes, as supported by the linear DMS measurements on FIGS. 2A and 2B since the 9 kHz out-of-phase peak is located between the two frequencies.

Figure 4A:
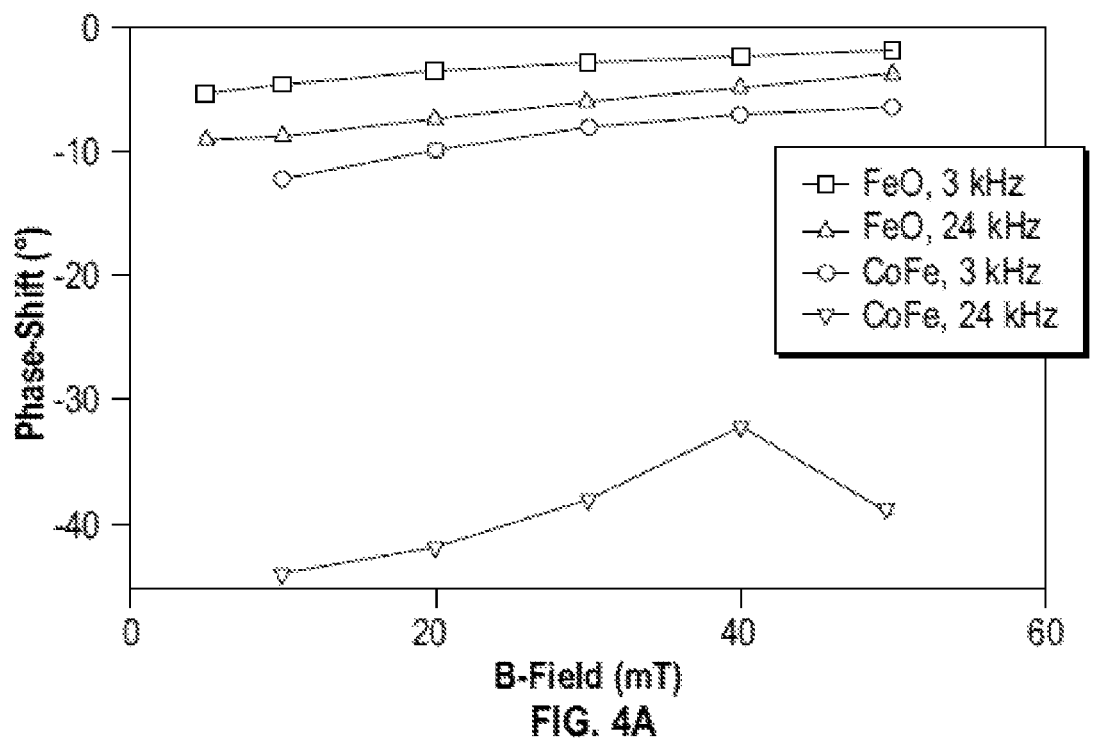
FIG. 4A is a graph of nonlinear phase shifts obtained for iron oxide and cobalt ferrite according to various embodiments of the present disclosure.
Figure 4B:
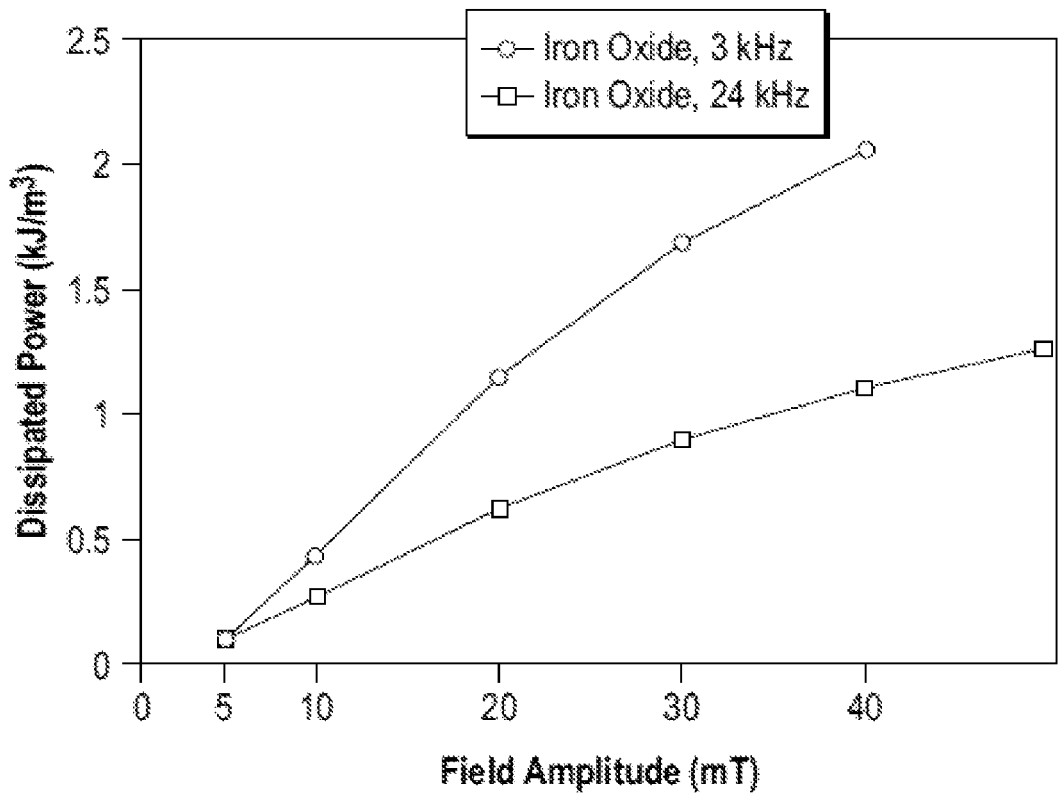
FIG. 4B is a graph of dissipated energies obtained for iron oxide according to various embodiments of the present disclosure.

With reference to FIG. 4A, shown is a graph of nonlinear MPS phase shifts obtained for iron oxide and cobalt ferrite. Particularly, FIG. 4A compares the phase shift between the instantaneous magnetization and the magnetic field for all field amplitudes and frequencies. While increasing the magnetic field amplitude, the magnetic torque increases, shortening the relaxation time and diminishing the phase shift. Increasing the frequency increases the hydrodynamic torque and thus the phase shift. The phase shift change from 3 kHz to 24 kHz is relatively small for iron oxide, but dramatically larger for cobalt ferrite, supporting the dramatic behavior change with the frequency. The direct effect of the phase shift is the appearance of a magnetization curve opening, i.e. a non-zero dynamic remanence and coercivity in the dynamic magnetization curve. As a consequence, curve openings in FIGS. 3B and 3D are larger at 24 kHz than at 3 kHz and larger for cobalt ferrite than for iron oxide. Moreover, the phase shift and consequently the magnetization curve opening are related to dissipation phenomena. FIG. 4B presents the dissipated energy for all experiments. The dissipated energy is higher at higher field frequencies and amplitudes.

Figure 5A:
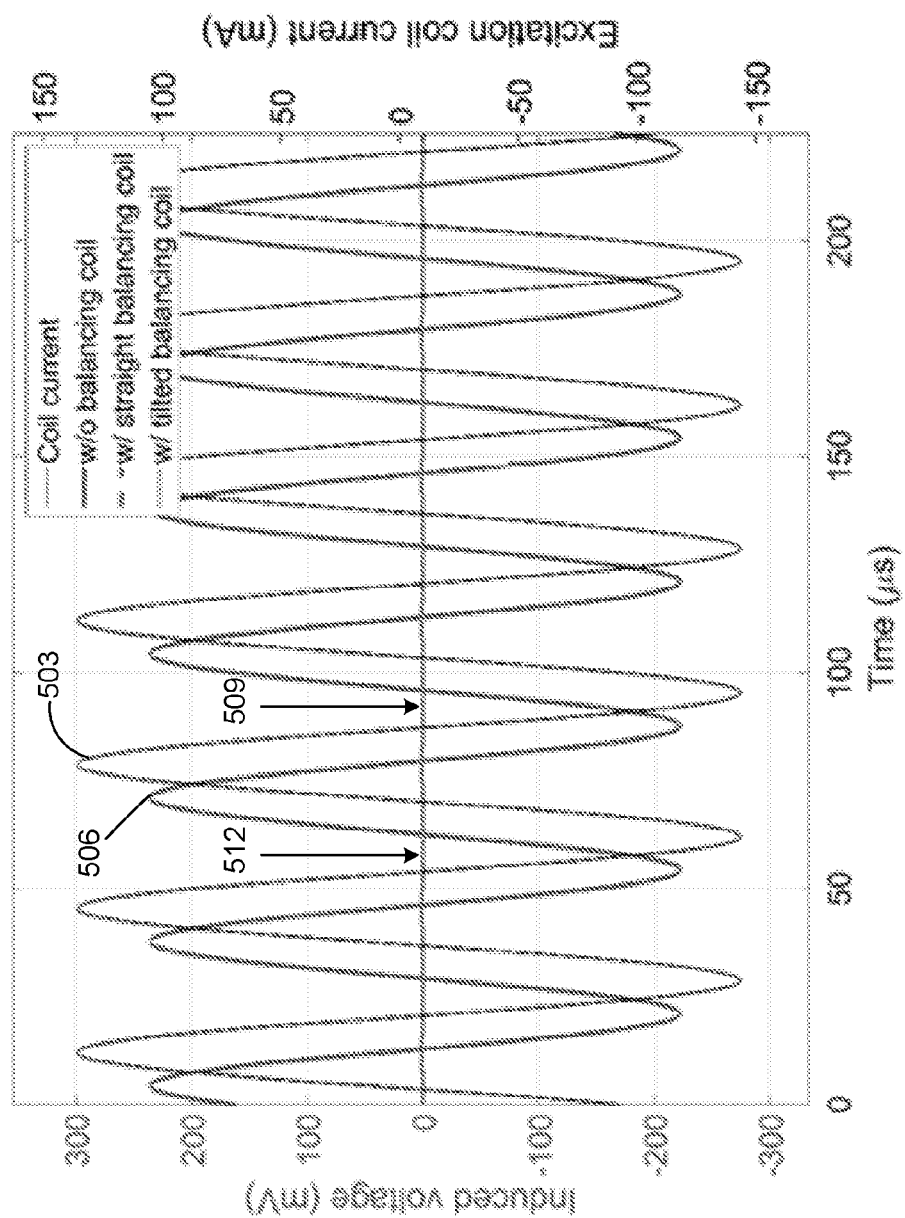
FIGS. 5A and 5B are graphs of balancing coil characterizations of a titling balancing coil embodiment according to various embodiments of the present disclosure.
Figure 5B:
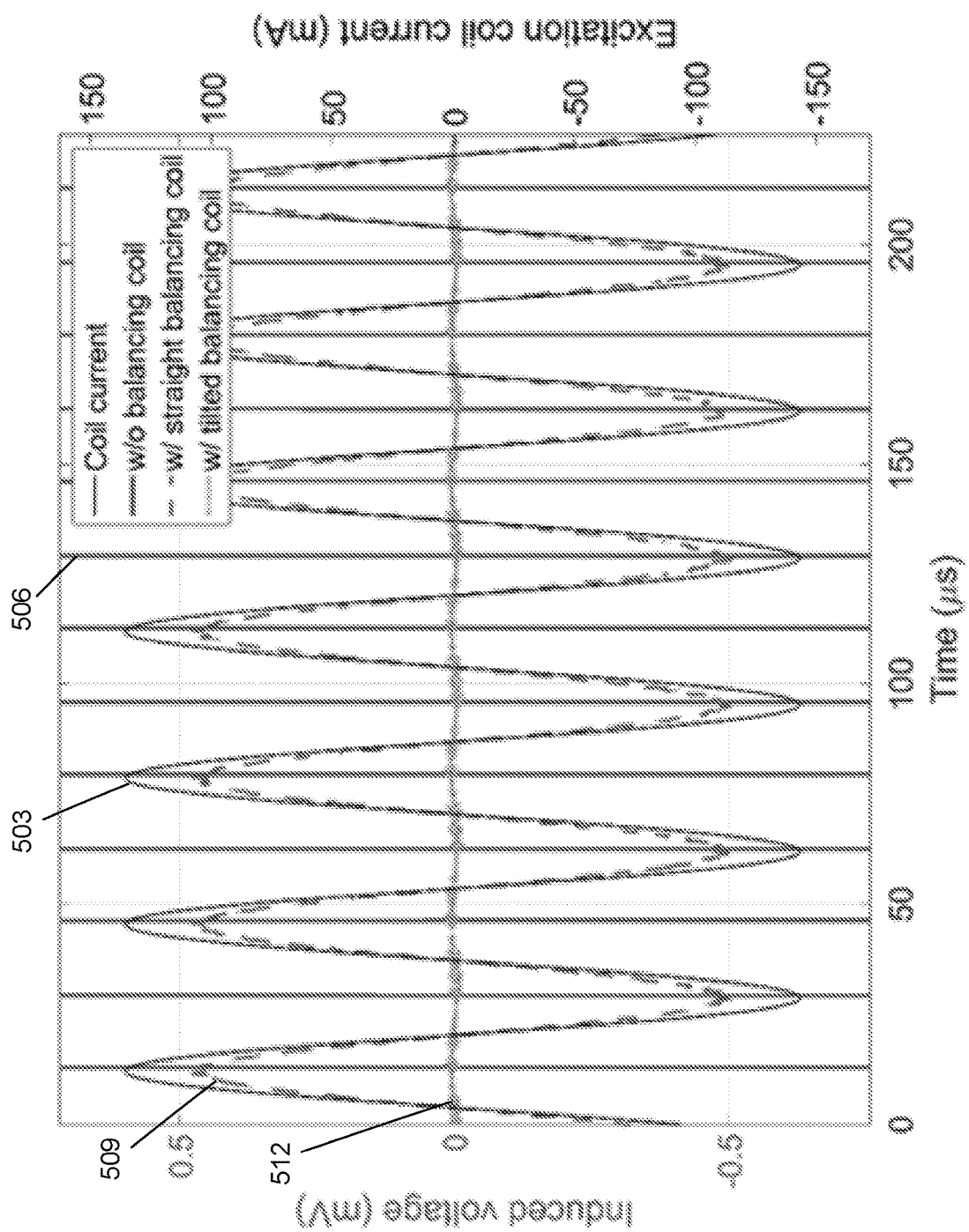

With reference to FIGS. 5A and 5B, shown are graphs of balancing coil characterizations of a titling balancing coil embodiment, as illustrated in FIG. 1D. FIG. 5B represents an enlarged view of portions of the signals shown in FIG. 5A. Referring between FIGS. 5A and 5B, reference number 503 points to a coil current signal and reference number 506 points to an induced voltage signal without a balancing coil 506. Reference number 509 points to an induced voltage signal with a straight balancing coil and reference number 512 points to an induced voltage signal with a titled balancing coil. For a characterization of about 140 m A of current, the direct excitation coil to pick-up coil feed-through is reduced 466× (−53 dB) by the straight balancing coil and 45800× (−93 dB) by the tilted balancing coil. Note the $\pi/2$ phase-shift for direct induction, and 0 phase-shift for the remaining feed-through after balancing.

The embodiments of the present disclosure relate to the design and validation of a magnetic particle spectrometer to characterize the linear and nonlinear behavior of magnetic nanoparticle suspensions. The present disclosure describes the various components of the MPS system 103 and the post-processing and calibration procedures. Linear DMS measurements at 1 mT were realized in a wide frequency range (0.5-120 kHz) showing good agreement with a commercial AC susceptometer. Nonlinear MPS measurements can require resonant and matching circuits to apply 50 mT at discrete frequencies from 3 kHz to 24 kHz. The sensing coil system 109 and the feed-through cancellation procedure can enable fine measurements up to 50 harmonics. As non-limiting examples, two MPS modes were tested for iron oxide and cobalt ferrite suspensions, which exhibit very different magnetic relaxation behaviors. The measured time varying induced voltage, the voltage FFT, and the reconstructed instantaneous magnetization analysis were used to assess the magnetic suspension rotational dynamics and to investigate their relaxation and saturation effects.

It is emphasized that the above-described embodiments of the present disclosure are merely non-limiting examples of possible implementations to set forth a clear understanding of the principles of the disclosure. Many variations and modifications can be made to the above-described embodiments without departing substantially from the spirit and principles of the disclosure. All such modifications and variations are intended to be included herein within the scope of this disclosure.

Therefore, the following is claimed:

1. An apparatus, comprising:
an electrical source configured to generate a time-varying current supply;
an excitation coil coupled to the electrical source to generate a time-varying magnetic field based on the time-varying current supply for application to a magnetic sample;
a sensing coil system that senses a magnetic response of the magnetic sample, the magnetic response comprising an induced voltage generated in response to the time-varying magnetic field, the sensing coil system comprising a pick-up coil and a balancing coil to cancel a portion of the time-varying magnetic field that is induced from the excitation coil into the pick-up coil, the sensing coil system comprising a mechanically adjustable fine-tuning coil that modifies an effect of the cancellation of the time-varying magnetic field induced from the excitation coil, the adjustable fine-tuning coil being electrically coupled with the pick-up coil and the balancing coil; and a data acquisition system that measures the induced voltage generated by the sensing coil system.

2. The apparatus of claim 1, wherein the excitation coil is a gapped solenoid excitation coil.

3. The apparatus of claim 1, wherein the data acquisition system further comprises a magnetic field sensor that measures the time-varying magnetic field.

4. The apparatus of claim 1, further comprising a structure to tilt the balancing coil with respect to a tilt axis to modify an amount of the cancellation of the induction from the excitation coil.

5. The apparatus of claim 1, wherein the pick-up coil is internally molded in epoxy resin to minimize a distance between the pick-up coil and the magnetic sample.

6. The apparatus of claim 1, wherein the balancing coil is coupled in series with the pick-up coil, and the balancing coil is wound in a direction opposition of the pick-up coil.

7. The apparatus of claim 1, wherein the data acquisition system is configured to measure the time-varying current supply to assess a reference phase of the time-varying magnetic field.

8. The apparatus of claim 1, further comprising a resonant matching circuit coupled to the electrical source.

9. A magnetic particle spectrometer, comprising:
an electrical source configured to generate a time-varying current supply;
an excitation coil system coupled to the electrical source to generate a time-vary magnetic field for application to a sample;
a sensing coil system that senses a magnetic response of the sample in response to the time-varying magnetic field, wherein the sensing coil system comprises a pick-up coil and a balancing coil that can be translated or rotated, the balancing coil being configured to cancel a feed-through induction signal, wherein the sensing coil system comprising a mechanically adjustable fine-tuning coil that modifies an effect of the cancellation of the feed-through induction signal from the excitation coil system, the adjustable fine-tuning coil being electrically coupled with the pick-up coil and the balancing coil; and
a data acquisition system that measures the magnetic response from the sensing coil system.

10. The magnetic particle spectrometer of claim 9, wherein:
the magnetic response is representative of a magnetization change of the sample based on the time-varying magnetic field; and
the magnetic response generates an inducted voltage in the sensing coil system.

11. The magnetic particle spectrometer of claim 9, wherein the balancing coil is translated or rotated to modify an amount of the cancellation of the feed-through induction signal.

12. The magnetic particle spectrometer of claim 9, wherein the excitation coil system is coupled to the electrical source via a resonant matching circuit.

13. The magnetic particle spectrometer of claim 12, wherein the resonant matching circuit comprises at least one pair of capacitors designed for a current gain greater than one at a plurality of discrete frequencies in a non-linear mode.

14. The magnetic particle spectrometer of claim 9, wherein the excitation coil system comprises a plurality of coils with different orientations to generate a rotating magnetic field.

15. A system, comprising:
an electrical source configured to generate a time-varying current supply;
an excitation coil coupled to the electrical source to generate a time-varying magnetic field based on the time-varying current supply for a magnetic sample; and
a sensing coil system to detect an induced voltage from a magnetic response of the magnetic sample in response to the time-varying magnetic field, the sensing coil system comprising a pick-up coil and a balancing coil to cancel a feed-through induced signal, the sensing coil system comprising a mechanically adjustable tuning coil that is magnetically coupled to the pick-up coil and the balancing coil, the adjustable tuning coil being configured to adjust the cancellation of the feed-through induced signal.

16. The system of claim 15, further comprising a structure to rotate the balancing coil with respect to an axis to adjust the cancellation of the feed-through induced signal.

17. The system of claim 15, wherein the excitation coil is coupled to the electrical source via a resonant matching circuit.

18. The system of claim 15, wherein the excitation coil is directly coupled to the electrical source.

19. The system of claim 15, further comprising a data acquisition system that measures, records, and applies signal processing techniques to the induced voltage from the sensing coil system.

20. The system of claim 15, wherein the adjustable tuning coil is mechanically rotated to adjust the cancellation of the feed-through induced signal.

* * * * *